US008249692B2

United States Patent
Vilsmeier et al.

(10) Patent No.: US 8,249,692 B2
(45) Date of Patent: Aug. 21, 2012

(54) METHOD AND DEVICE FOR IMAGE OPTIMIZATION IN ULTRASOUND RECORDINGS

(75) Inventors: Stefan Vilsmeier, Kufstein (AT); Alexander Pfäffle, Erding (DE); Robert Schmidt, München (DE)

(73) Assignee: Brainlab AG, Feldkirchen (DE)

( * ) Notice: Subject to any disclaimer, the term of this patent is extended or adjusted under 35 U.S.C. 154(b) by 1459 days.

(21) Appl. No.: 10/830,731

(22) Filed: Apr. 23, 2004

(65) Prior Publication Data

US 2004/0215073 A1    Oct. 28, 2004

Related U.S. Application Data

(60) Provisional application No. 60/489,754, filed on Jul. 24, 2003.

(30) Foreign Application Priority Data

Apr. 25, 2003 (EP) .................................... 03008841

(51) Int. Cl.
*A61B 5/00* (2006.01)
*A61B 8/00* (2006.01)
(52) U.S. Cl. .................. 600/427; 600/411; 600/443

(58) Field of Classification Search .................. 600/407, 600/411, 424, 427, 437, 443
See application file for complete search history.

(56) References Cited

U.S. PATENT DOCUMENTS

| 5,526,814 | A | * | 6/1996 | Cline et al. ...................... 600/411 |
| 5,938,600 | A | * | 8/1999 | Van Vaals et al. .............. 600/411 |
| 6,138,495 | A | | 10/2000 | Paltieli et al. ................... 73/1.86 |
| 6,423,006 | B1 | | 7/2002 | Banjanin ........................ 600/453 |
| 6,438,405 | B1 | * | 8/2002 | Mooney et al. ................ 600/427 |
| 6,459,925 | B1 | * | 10/2002 | Nields et al. ................... 600/427 |
| 2001/0034484 | A1 | * | 10/2001 | Nakamura et al. ............. 600/443 |

FOREIGN PATENT DOCUMENTS

| EP | 0 985 380 A1 | 3/2001 |
| EP | 1 152 372 A2 | 7/2001 |
| EP | 1 264 577 A1 | 11/2002 |

* cited by examiner

*Primary Examiner* — Ruth S Smith
(74) *Attorney, Agent, or Firm* — Renner, Otto, Boisselle & Sklar, LLP

(57) ABSTRACT

A device for positioning at least one ultrasound probe of an ultrasound apparatus can include a recording device for recording an object and an evaluating unit that evaluates data corresponding to the object obtained from the recording device. A computational unit can generate positional data for the at least one ultrasound probe of the ultrasound apparatus. The device can be used for setting at least one parameter of the ultrasound apparatus based on data obtained by the recording device.

15 Claims, 1 Drawing Sheet

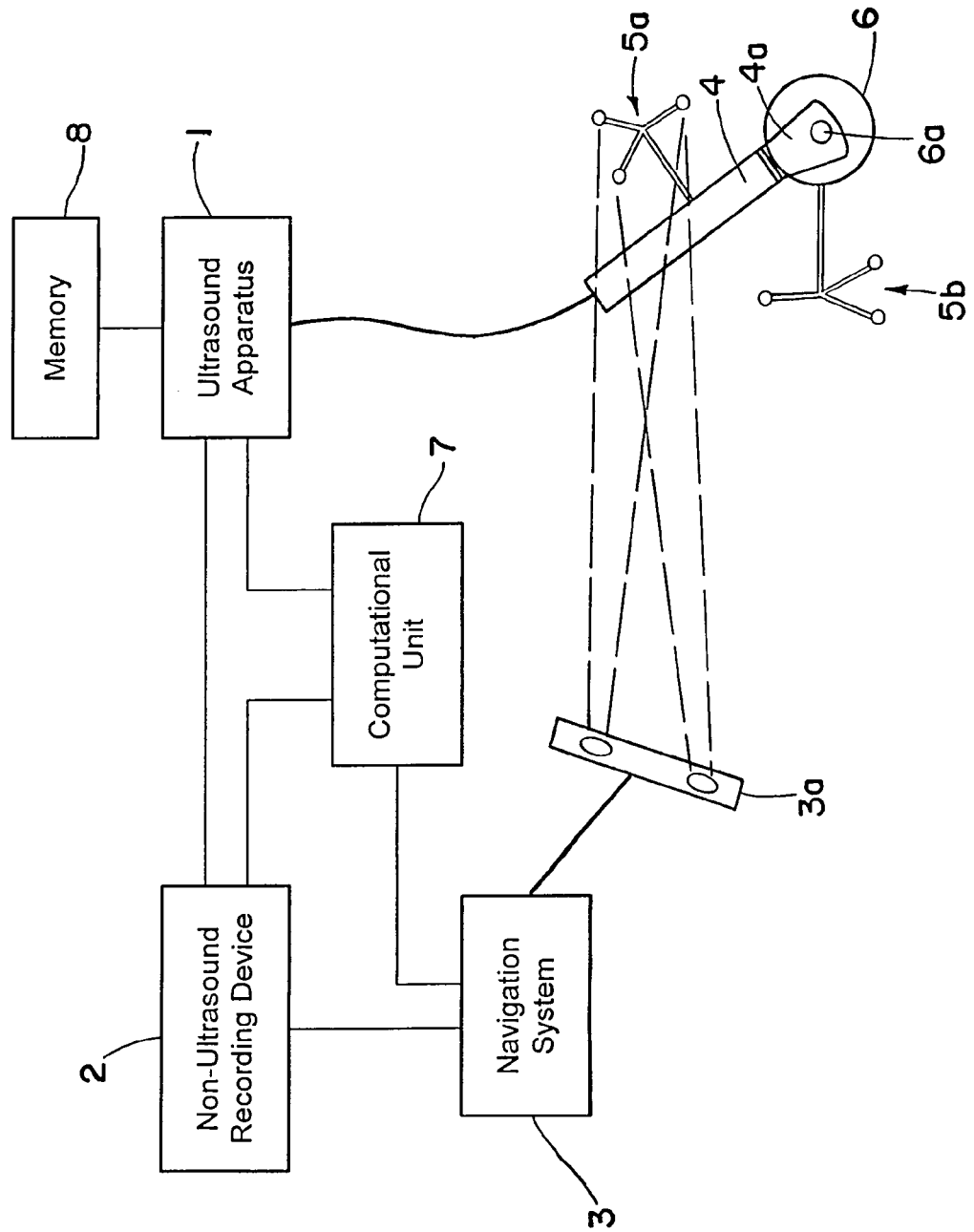

METHOD AND DEVICE FOR IMAGE OPTIMIZATION IN ULTRASOUND RECORDINGS

RELATED APPLICATION DATA

This application claims priority of U.S. Provisional Application No. 60/489,754, filed on Jul. 24, 2003, which is incorporated herein by reference in its entirety.

FIELD OF THE INVENTION

The present invention relates to methods and devices for image optimization in ultrasound recordings. In particular, the invention relates to methods and devices for automatically setting an ultrasound apparatus and for positioning an ultrasound probe.

BACKGROUND OF THE INVENTION

Modern ultrasound apparatuses have a multitude of mapping modes with a multitude of parameters to be set. For example, the SONOLINE® Omnia ultrasound system produced by SIEMENS® has imaging functions in B-mode and M-mode, wherein, for example, various duplex functions and color duplex imaging methods can be set. In the B-mode type of imaging (B for "brightness"), a recorded image is generated in a two-dimensional grey-scale representation, where the brightness of a pixel of the generated image depends on the intensity of the reflected sound. In color duplex operation, a defined window or a range of interest (ROI) in the B-image is assigned a color, wherein the depth, position and size of the window, as well as various parameters relating to coloring, can be set in order to visually represent the movement of a liquid, such as, for example, blood, or tissue. In this way, the flow of blood in the heart or in vessels can be measured using the Doppler effect.

However, a multitude of parameters have to be manually set on an ultrasound apparatus in order to zoom in on a range of interest, such as, for example bones, vessels or a particular area of tissue. Setting an ultrasound apparatus in this way is relatively time-consuming and can only be performed with appropriate experience, such that the optimally achievable image quality of a range of interest cannot always be generated. Examples of parameters to be set on an ultrasound apparatus include the depth of sound, depth gain compensation, dynamic range, contour, focus, image rate or line density, frequency, amplification, grey scales, transmitting output, post-processing curves for optimizing the grey scales, setting the sector angle or image width or setting a zoom. Further settings have to be made, for example, for optimizing three-dimensional images.

Various methods for setting parameters of an ultrasound apparatus are known from U.S. Pat. No. 6,322,509 B1 and the prior art described therein. With respect to the general functionality of an ultrasound apparatus and with respect to the parameters to be set on an ultrasound apparatus, reference is made to U.S. Pat. No. 6,322,509 B1 and to the operating manual of the SONOLINE® Omnia ultrasound system by SIEMENS®, whose teachings are incorporated into this application by reference in their entireties.

SUMMARY OF THE INVENTION

One object of the present invention includes methods and devices for optimizing the images generated by ultrasound apparatus.

In accordance with one aspect of the invention, the invention relates to a method for setting or fixing at least one setting parameter of an ultrasound apparatus, wherein the object or body from which an ultrasound image of at least a partial area of the object is to be generated is recorded using an imaging method, such as nuclear spin resonance (MRI) recording, computer tomography, PET, SPECT or an x-ray recording or fluoroscopy. In one embodiment, an imaging recording method is performed, which is not based on ultrasound recordings, since using the aforementioned recording methods, the three-dimensional structure of an object or body can be ascertained relatively simply. From the data of the object or of a partial area of it, thus obtained, data, such as, for example, image data, are generated, which can be the basis for object-specifically or body-specifically setting at least one setting parameter of the ultrasound apparatus. Using an MRI recording, for example, it can be ascertained where a range of interest (ROI) lies, such that, for example, the transmitting output, depth gain compensation, amplification and/or other parameters of the ultrasound apparatus can be set such that the range of interest is displayed with as high or optimal an image quality as possible.

If, for example, the course of blood vessels, the position of diseased tissue, such as, for example, a tumor, or the position of bones in a body is to be displayed using the ultrasound apparatus, then information with respect to the structure to be mapped in the body, such as, for example, the distance of the structure or the range of interest from the surface of the body or the course of structure in the body, can be obtained from a recording taken beforehand using an imaging method. From the recording, settings can be ascertained or calculated for parameters of the ultrasound apparatus, in order to display the range of interest (ROI) with as high an image quality as possible. Manually setting and re-adjusting the ultrasound apparatus is therefore not required, since, for example, all the parameter values required for setting the ultrasound apparatus can be ascertained from the recording of the object or the body to be examined, performed beforehand. It is therefore possible to automatically, body-specifically initialize and/or set an ultrasound apparatus.

According to another embodiment, the invention relates to a method for positioning at least one ultrasound probe on a body or object to be examined. The object can be recorded using an imaging method and image data are can be generated from the recording data, where the image data provides information on where one or more ultrasound probes can be particularly advantageously or as optimally as possible positioned, so that one or more ultrasound images can be generated with as high a quality as possible. The information with respect to the most optimal position possible of at least one ultrasound probe can, for example, be output in the form of an absolute variable, for example, as information that the the position is a given distance above the navel. It is equally possible to use known navigation and tracking methods to position a probe as optimally as possible on the object or body to be examined. To this end, reflective markers can be attached in a known way to the at least one ultrasound probe and to the object or body to be examined, enabling the probe to be navigated relative to the body and positioned at the desired optimal point.

In one embodiment, generating at least one setting value for at least one setting parameter of the ultrasound apparatus can be combined with positioning at least one ultrasound probe as advantageously as possible, wherein data provided by recording the object to be examined using the ultrasound apparatus and an imaging method are respectively accessed for these methods.

The ultrasound apparatus can be set such that parameters of the ultrasound apparatus are selected, depending on the position of the ultrasound probe and based on the image data corresponding to the position, such that an ultrasound image, which is as optimal as possible with respect to the position of the ultrasound probe, can be generated.

In one embodiment, it is possible to select or change the parameters for setting the ultrasound apparatus, such that a setting of the ultrasound apparatus with respect to the position of an ultrasound probe on an object to be examined, ascertained, for example, by a navigation system, is obtained using recording data. This enables a range of interest to be displayed with as high an image quality as possible. If, for example, the navigation system identifies a change in the position or shift of an ultrasound probe relative to an object to be examined, it is possible to automatically change the setting parameters of the ultrasound apparatus such that a range of interest can always be clearly displayed.

Data can be output from the ultrasound apparatus, which can be used for positioning the ultrasound probe. On the basis of the images recorded by an ultrasound probe, for example, it can be ascertained whether the probe is correctly positioned or whether the probe still has to be moved in a particular direction. In this way, information can be obtained from the image data recorded by the probe as to how the probe must be navigated in order to be correctly positioned.

In order to ascertain values of the setting parameters for mapping a desired area, specific object-dependent or object-typical information with respect to the desired areas to be mapped is accessed. For example, a first parameter set can be pre-set, which enables the ultrasound apparatus to be set for displaying blood vessels, and a second parameter set can be pre-set which is advantageous for displaying bones, particular tissue structures, such as, for example, tumors or other structures of interest, which may be selected by a user. Equally, other parameter sets for displaying areas or body structures, which are respectively of interest can be pre-set, which enable an image of a particular area of tissue of interest to be generated with as high a quality as possible.

The invention further relates to a computer program which, when it is loaded onto a computer or run on a computer, performs at least one of the method steps described above. Furthermore, the invention relates to a program storage medium or computer program product comprising such a program.

In accordance with another aspect, the invention relates to a device for setting at least one setting parameter of an ultrasound apparatus for generating an ultrasound recording of an object, including a recording device for recording the object. An imaging method can be performed using the recording device in order to examine an object. Recording devices that may be used in accordance with the invention include devices that are suitable for performing the recording methods described above, such as for example MRI, CT, PET, SPECT or fluoroscopy. Furthermore, the device in accordance with the invention can include an evaluating or computational unit that can ascertain at least one setting of a setting parameter of the ultrasound apparatus from the recording data of the object, in order, for example, to be able to display or map a desired pre-set area as clearly as possible using the ultrasound apparatus.

Furthermore, the invention relates to a device for positioning at least one ultrasound probe. The device can include at least one recording device as described above and an evaluating or computational unit which ascertains a position for the ultrasound probe on the body or object to be examined using the ultrasound apparatus from the recording data, such that at least one ultrasound probe can be positioned as optimally as possible on or on top of the body or object to be examined.

In one embodiment, it is possible to combine both devices, such that at least one value of a setting parameter can be ascertained from recording data of an object or body to be examined, obtained from imaging methods, and a position for at least one ultrasound probe can be ascertained.

In a device in accordance with the invention, a tracking or navigation system can be provided in order to be able to move at least probe as precisely as possible to a desired position on or on top of the object to be examined.

A memory can be provided in which parameter sets for setting an ultrasound apparatus are stored in order, for example, to initialize or set an ultrasound apparatus such that it is optimized for mapping particular structures or a particular tissue, such as, for example, vessels or muscles. These parameter sets can be used together with data ascertained object-specifically or body-specifically to obtain an optimal setting of an ultrasound apparatus for mapping a particular area.

The invention further relates to a system including at least one device as described above and one ultrasound apparatus which can be coupled to the at least one device via an interface in order, for example, to transmit parameters for setting the ultrasound apparatus, image data or positional data for arranging at least one ultrasound probe.

BRIEF DESCRIPTION OF THE DRAWINGS

These and further features of the present invention will be apparent with reference to the following description and drawings, wherein:

FIG. 1 is a diagrammatic illustration of a device in accordance with the invention, using which a method in accordance with the invention can be performed.

DETAILED DESCRIPTION OF THE INVENTION

FIG. 1 shows an ultrasound apparatus 1 connected to an ultrasound probe 4, which has a settable detecting and mapping area 4a. A range of interest 6a is arranged in the interior of a body 6 and is to be detected by the ultrasound apparatus 1 and displayed with a high image quality. To this end, the body 6 can be recorded by examination using the ultrasound apparatus 1. A non-ultrasound recording device 2, such as, for example, a nuclear spin tomograph or MRI, can be used to obtain information related to the position and orientation of the range of interest (ROI) 6a within the body 6. Alternatively, the recording device can include any of CT, PET, SPECT and fluoroscopy imaging devices. An evaluating or computational unit 7 can ascertain how far the range of interest 6a is below one or more particular surface points on the body 6.

The data obtained by the recording device 2 can be transmitted, directly or after being evaluated by the unit 7, to a navigation system 3 connected to an IR camera 3a. An exemplary navigation system is described more fully in co-owned U.S. Pat. No. 6,351,659, which is incorporated herein by reference in its entirety. By means of the navigation system 3, and using a marker 5a connected to the ultrasound probe 4 and a marker 5b connected to the body 6, the ultrasound probe 4 can be positioned at a desired point on or on top of the body 6. It is to be appreciated that the markers 5a, 5b can include reference starts or other appropriate markers.

The image data of the body 6 obtained by the recording device 2 can be evaluated and/or converted by the computational unit 7. In one embodiment, the evaluated and/or converted image data can be used to ascertain where a range of interest (ROI) lies, such that, for example, the transmitting output, depth gain compensation, amplification and/or other parameters of the ultrasound apparatus 1 can be set such that the range of interest is displayed with as high or optimal an image quality as possible. In one embodiment, the evaluated and/or converted image data can be used as parameters for setting the ultrasound apparatus 1 so that the range of interest 6a in the interior of the body 6 can be detected by the ultrasound probe 4 placed at a particular position, such that the range of interest 6a is within the detecting and recording area 4a of the ultrasound probe 4, such that the range of interest 6a can be displayed with a high or optimal image quality.

A memory 8 can store parameter data sets for the ultrasound apparatus 1 which can be used for displaying particular structures, such as, for example, blood vessels, the brain, muscles or bones. In one embodiment, a user can select from a pre-set menu that he wishes to display blood vessels using the ultrasound apparatus 1, whereupon the probe 4 is positioned on the body 6 using the navigation system 3 and the ultrasound apparatus 1 is set based on the body-specific recording data of the recording device 2 and from the memory 8 the parameter data suitable for blood vessels, such that the blood vessel running within the body 6 are displayed with a high or optimal image quality.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer program stored on a non-transitory machine-readable medium, wherein when the program is loaded onto a memory of a computer and executed, causes the computer to:
   receive non-ultrasound patient data from a non-ultrasound recording device;
   receive position data related to a position of an ultrasound apparatus relative to a patient;
   evaluate the non-ultrasound patient data; and
   generate and dynamically update a value of at least one ultrasound imaging parameter based on the non-ultrasound patient data and the received ultrasound position value to optimize an ultrasound image based on the position of the ultrasound apparatus relative to the patient, the at least one ultrasound imaging parameter including a parameter other than a position of the ultrasound apparatus.

2. The computer program as set forth in claim 1, wherein the ultrasound imaging parameter includes color, depth, depth gain compensation and/or dynamic range.

3. The computer program as set forth in claim 1, wherein the ultrasound imaging parameter includes contour, focus and/or image rate/line density.

4. The computer program as set forth in claim 1, wherein the ultrasound imaging parameter includes frequency, amplification, grey scales, offset, transmitting output and/or correlation.

5. The computer program as set forth in claim 1, wherein the ultrasound imaging parameter includes post-processing curves for grey scales, sector angle, image width, type of sound heard and/or zoom.

6. A device for setting at least one parameter of an ultrasound apparatus, the device comprising:
   a computer comprising memory; and
   a computer program stored in the memory, wherein when executed by the computer the program causes the computer to:
   receive non-ultrasound patient data from a non-ultrasound recording device;
   receive position data related to a position of an ultrasound apparatus relative to a patient;
   evaluate the non-ultrasound patient data; and
   generate and dynamically update a value of at least one ultrasound imaging parameter based on the non-ultrasound patient data and the received ultrasound position value to optimize an ultrasound image based on the position of the ultrasound apparatus relative to the patient, the at least one ultrasound imaging parameter including a parameter other than a position of the ultrasound apparatus.

7. A system comprising the device set forth in claim 6 and a non-ultrasound recording device.

8. The system as set forth in claim 7, wherein the non-ultrasound recording device includes an (i) MRI, (ii) CT, (iii) PET, (iv) SPECT or (v) fluoroscopy recording device.

9. The system according to claim 7, further comprising:
   a navigation system;
   an ultrasound apparatus including a probe; and
   parameter data sets stored in memory and corresponding to body structures of the patient, wherein based on a selected parameter of the parameter data sets, the probe is positioned on the patient using the navigation system.

10. A computer program stored on a non-transitory machine-readable medium, wherein when the program is loaded onto a memory of a computer and executed, the program causes the computer to, in response to receipt of non-ultrasound patient data from a non-ultrasound recording device and position data related to a position of an ultrasound apparatus relative to a patient:
    evaluate the non-ultrasound patient data; and
    generate and dynamically update a value of at least one ultrasound imaging parameter based on the non-ultrasound patient data and the received ultrasound position value to optimize an ultrasound image based on the position of the ultrasound apparatus relative to the patient, the at least one ultrasound imaging parameter including a parameter other than a position of the ultrasound apparatus.

11. The computer program as set forth in claim 10, wherein the ultrasound imaging parameter includes color, depth, depth gain compensation and/or dynamic range.

12. The computer program as set forth in claim 10, wherein the ultrasound imaging parameter includes contour, focus and/or image rate/line density.

13. The computer program as set forth in claim 10, wherein the ultrasound imaging parameter includes frequency, amplification, grey scales, offset, transmitting output and/or correlation.

14. The computer program as set forth in claim 10, wherein the ultrasound imaging parameter includes post-processing curves for grey scales, sector angle, image width, type of sound heard and/or zoom.

15. The computer program as set forth in claim 10, wherein the non-ultrasound patient data comprises patient image data.

* * * * *